United States Patent

Opitz et al.

[11] 4,323,517
[45] Apr. 6, 1982

[54] METHOXY AND METHYLSULFINYLTHIOLESTERS

[75] Inventors: Wolfgang Opitz; Eugen Etscherberg, both of Cologne; Hans-Dieter Dell, Berg. Gladbach; Haireddin Jacobi, Leichlingen, all of Fed. Rep. of Germany

[73] Assignee: Troponwerke GmbH & Co. KG, Cologne, Fed. Rep. of Germany

[21] Appl. No.: 182,353

[22] Filed: Aug. 29, 1980

Related U.S. Application Data

[62] Division of Ser. No. 963,651, Nov. 24, 1978, Pat. No. 4,246,278.

[30] Foreign Application Priority Data

Dec. 2, 1977 [DE] Fed. Rep. of Germany ....... 2753786
Jun. 3, 1978 [DE] Fed. Rep. of Germany ....... 2824386

[51] Int. Cl.³ .......................................... C07C 153/017
[52] U.S. Cl. ................................................ 260/455 R
[58] Field of Search ..................................... 260/455 R

[56] References Cited

U.S. PATENT DOCUMENTS 2,259,869 10/1941 Allen .................................... 424/301
3,346,611 10/1967 Doss ................................ 260/455 R Primary Examiner—Henry R. Jiles
Assistant Examiner—Robert C. Whittenbaugh Attorney, Agent, or Firm—Sprung, Felfe, Horn, Lynch & Kramer

[57] ABSTRACT

The present invention provides, inter alia, antiphlogistically effective agents, including pharmaceutical compositions containing said agents. Also included are methods for the use of said agents. The active compounds are those of the formula

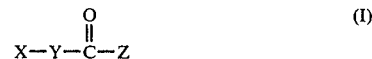

or an ester thereof, in which X denotes a hydrogen atom, an alkyl group, an alkoxy group, an alkylthio group, an alkylsulphinyl or alkylsulphonyl group or a hydroxyl or mercapto group, Y denotes a grouping

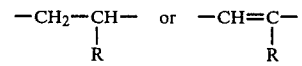

in which R denotes a hydrogen atom or an alkyl group, and Z denotes a hydroxyl group or an alkoxy or alkylthio group, at least one of the substituents X or Z in each case denoting a sulphur-containing radical.

3 Claims, No Drawings

METHOXY AND METHYLSULFINYLTHIOLESTERS

This is a division of application Ser. No. 963,651, filed Nov. 24, 1978, now U.S. Pat. No. 4,246,278.

The present invention relates to the use as antiphlogistic agents of certain sulphur-containing organic acids and their esters, some of which are known.

The use of these sulphur-containing organic acids and esters of this class of compounds as medicaments is not known.

According to the present invention there is provided a pharmaceutical composition containing as an active ingredient a compound which is a sulphur-containing carboxylic acid of the following general formula

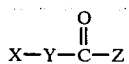

or an ester thereof, in which
X denotes a hydrogen atom, an alkyl group, an alkoxy group, an alkylthio group, an alkylsulphinyl or alkylsulphonyl group or a hydroxyl or mercapto group,
Y denotes a grouping

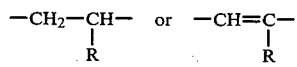

in which
R denotes a hydrogen atom or an alkyl group, and
Z denotes a hydroxyl group or an alkoxy or alkylthio group, at least one of the substituents X or Z in each case denoting a sulphur-containing radical,
in admixture with a solid or liquefied gaseous diluent or in admixture with a liquid diluent other than a solvent of molecular weight less than 200 except in the presence of a surface-active agent.

Some of the compounds of the general formula (I) claimed as active compounds for medicaments are known and some are commercially available.

Most of the compounds according to the invention were prepared according to the equation which follows, as may be shown using an example:

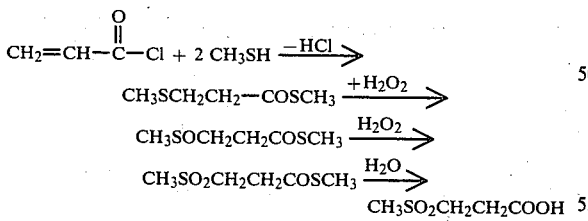

Depending on the concentration of the oxidising agent and depending on the reaction time used, the individual oxidation stages can be isolated, or mixtures are formed which can be separated by chromatography, as is described in detail in the experimental section.

Those compounds which are in free acid form can, of course, form salts, particularly with alkali and alkaline earth metals, such as sodium, potassium, calcium, etc.

Surprisingly, the sulphur-containing carboxylic acids and esters according to the invention exhibit a substantially greater therapeutic range, coupled with a very good anti-inflammatory action, than the compounds hitherto known in this field. Furthermore, they have fewer side-effects, such as for example, heartburn. The formation of ulcers, intestinal haemorrhages and the like. The compounds according to the invention thus represent an advance in pharmacy.

In detail, examples which may be mentioned of the compounds which can be used according to the invention are: 3-methylsulphinylpropionic acid ($CH_3SOCH_2CH_2COOH$), S-methyl methacrylthioate ($CH_2=C(CH_3)COSCH_3$). S-methyl crotonylthioate ($CH_3CH=CH-COSCH_3$), S-ethyl acrylthioate ($CH_2=CH-COSC_2H_5$). S-ethyl 3-ethyl-thiopropionylthioate ($C_2H_5SCH_2COSC_2H_5$). S-methyl 3-methylthio-2-propylcarbonylthioate ($CH_3SCH_2CH(CH_3)COSCH_3$), 3-mercaptopropionic acid ($HS-CH_2CH_2COOH$), S-methyl 3-methylthiopropionothioate ($CH_3S-CH_2-CH_2-COSCH_3$), methyl 3-methylthiopropionate ($Ch_3S-CH_2-CH_2-COOCH_3$), S-methyl acrylthioate ($CH_2=CH-COSCH_3$), methyl 3-mercaptopropionate ($HS-CH_2-CH_2-COOCH_3$), 3-methyl thiopropionic acid ($CH_3SCH_2CH_2COOH$), ethyl 3-methylthiopropionate ($CH_3SCH_2CH_2COOC_2H_5$), S-propyl 3-propyl-thiopropionothioate ($C_3H_7SCH_2CH_2COSC_3H_7$), S-isopropyl 3-isopropylthiopropionothioate ($CH_3CH(CH_3)SCH_2CH_2-COSCH(CH_3)CH_3$), S-butyl 3-butyl-thiopropionothioate ($C_4H_9SCH_2CH_2COSC_4H_9$), S-sec.-butyl 3-sec.-butyl-thiopropionothioate ($CH_3CH_2CH(CH_3)SCH_2CH_2COSCH(CH_3)CH_2CH_3$), S-tert.-butyl 3-tert.-butylthiopropionothioate ($(CH_3)_3CSCH_2CH_2COSC(CH_3)_3$), S-isobutyl 3-isobutylthiopropionothioate ($CH_3CH(CH_3)CH_2SCH_2CH_2COSCH_2CH(CH_3)_2$), S-butyl 3-butylsulphinylpropionothioate ($C_4H_9SOCH_2CH_2COSC_4H_9$), S-sec.-butyl 3-sec.-butylsulphinylpropionothioate ($CH_3CH_2CH(CH_3)SOCH_2CH_2COSCH(CH_3)-CH_2CH_3$), S-isopropyl 3-isopropylsulphinylpropionothioate ($(CH_3)_2CHSOCH_2CH_2COSCH(CH_3)_2$), S-propyl 3-propylsulphinylpropionothioate ($C_3H_7SOCH_2CH_2COSC_3H_7$), S-ethyl 3-ethylsulphinylpropionothioate ($C_2H_5SOCH_2COSC_2H_5$), S-tert.-butyl 3-tert.-butylsulphinylpropionothioate ($(CH_3)_3CSOCH_2CH_2COSC(CH_3)_3$), S-ethyl 3-ethylsulphenylpropionothioate ($C_2H_5SO_2CH_2CH_2COSC_2H_5$), S-sec.-butyl 3-sec.-butylsulphonylpropionothioate ($CH_3CH_2CH(CH_3)SO_2=CH_2CH-2COSCH(CH_3)CH_2CH_3$), 3-tert.-butyl sulphonylpropionic acid ($(CH_3)_3CSO_2CH_2CH_2COOH$), S-isobutyl 3-isobutylsulphenylpropionothioate ($(CH_3)_2CHCH_2SO_2CH_2CH_2COSCH_2CH(CH_3)_2$), S-tert.-butyl 3-tert.-butylsulphonylpropionothioate ($(CH_3)_3CSO_2CH_2CH_2COSC(CH_3)_3$), 3-sec.-butyl sulphonylpropionic acid ($CH_3CH_2CH(CH_3)SO_2CH_2CH-2COOH$), S-butyl 3-butylsulphonylpropionothioate ($C_4H_9SO_2CH_2COSC_4H_9$), 3-butyl sulphonylpropionic acid ($C_4H_9SO_2CH_2CH_2COOH$), 3-isobutyl sulphonylpropionic acid ($(CH_3)_2CHCH_2SO_2CH_2CH_2COOH$), S-isopropyl 3-isopropylsulphenylpropionothioate ($(CH_3)_2CHSO_2CH_2CH_2COSCH(CH_3)_2$), S-propyl 3-propylsulphonylpropionothioate ($C_3H_7SO_2CH_2CH-2COSC_3H_7$) and S-methyl 3-methylsulphonylpropionothioate ($CH_3SO_2CH_2CH_2COSCH_3$).

The pharmacological action may be demonstrated using S-methyl 3-methylthiopropionothioate (designated A in the following text) as an example.

Substance A possesses a very pronounced antiphlogistic action and is outstandingly suitable for parenteral use. The anti-inflammatory action was detected in paw oedemas, caused by the administration of kaolin, in rats. The $ED_{50}$ value was 4.85 μmols/kg after intramuscular injection. This value clearly shows, also in comparison with the $ED_{50}$ values, determined by the same method, for known commercially available antiphlogistic agents (see Table 1), that compound A greatly inhibits experimental inflammation.

It is known that almost all non-steroidal antiphlogistic agents lead to damage to the mucous membrane of the gastrointestinal tract in warm-blooded animals. Tests were therefore carried out to discover whether compound A has an ulcerogenic action after intramuscular use.

A $ED_{50}$ of 256.41 μmols/kg was found in rats. From the difference in dose between the two $ED_{50}$ values it can be seen that, measured by these two criteria, compound A has a wide therapeutic range.

Furthermore, A also has an action on other inflammation models. The $ED_{50}$ values which follow are found (mg/kg; intramuscularly): formalin oedema 5.4, albumin oedema 6.3, yeast oedema 27.4, concanavalin oedema 3.4 and trypsin oedema 2.0.

These comments can be further reinforced by the determination of the acute toxicity of compound A in rats after intramuscular injection.

The $LD_{50}$ was 4,587 μmols/kg.

The large difference between this value and the $ED_{50}$ value for the kaolin oedema underlines the unexpected favourable therapeutic range for compound A. The above results are compared with the corresponding values for flufenamic acid, phenylbutazone and indometacin in the table. The prominant position of compound A in respect of its therapeutic range can be seen by comparing the figures in the last two columns of the table.

TABLE 1

Comparison of the therapeutic range
Rats

| Substance | Kaolin oedema $ED_{50}$ μmols/kg | Stomach ulcer $ED_{50}$ μmols/kg | $LD_{50}$ μmols/kg | Method of administration | Therapeutic range $ED_{50}$ ulcer / $ED_{50}$ kaolin oedema | $LD_{50}$ / $ED_{50}$ kaolin oedema |
|---|---|---|---|---|---|---|
| S-methyl 3-methylthio-propiono-thioate | 4.85 | 5.76* 256.41 3.38 50.9 | 429.18 172.41 78.7 | 4,587 4,255 3,065 | 4,950 intra-muscular | 52.86 | 945.77 |
| Flufenamic acid | 36.2 | 55.1 23.9 167.4 | 32.7 234.9 | 2,037 1,632 4.803 | oral | 1.52 | 56.27 |
| Phenyl-butazone | 122 | 181.6 92.8 3.9 | 145.0 21.0 | 3,217 2,317 85 | oral | 1.48 | 26.36 |
| Indo-metacin | 2.9 | 11.1 2.3 | 6.4 | 68 55 | oral | 3.81 | 23.44 |

*The data denote confidence ranges with a probable error of 5%.

In addition to the effects described for compound A, it could also be shown that the other derivatives (see Table 2) likewise have a powerful anti-inflammatory action. The minimum doses which still cause a clearly detectable effect on the paw oedema after the administration of kaolin are listed in Table 2.

TABLE 2

Antiphlogistic action
Rats, kaolin oedema, intramuscularly, n = 10/dose group

| Compound | Dose mg/kg | Inhibition in % of the controls ($ED_{50}$ in mg/kg) |
|---|---|---|
| $HSCH_2CH_2COOH$ | 20.00 | 8.5 |
| $C_2H_5SCH_2CH_2COSC_2H_5$ | 2.50 | 58.2 (3.75) |
| $CH_3CH=CHCOSCH_3$ | 12.50 | 16.0 |
| $CH_2=C(CH_3)COSCH_3$ | 5.00 | 21.8 |
| $CH_3SOCH_2CH_2COSCH_3$ | 3.12 | 10.2 (1.8) |
| $CH_3SCH_2CH(CH_3)COSCH_3$ | 0.65 | 16.6 (4.5) |
| $CH_2=CHCOSC_2H_5$ | 0.32 | 18.5 (1.5) |
| $CH_3SCH_2CH_2COOC_2H_5$ | 25 | 16 |
| $(CH_3)_3CSCH_2CH_2COSC(CH_3)_3$ | 12.5 | 23.3 |
| $(CH_3)_2CHSCH_2CH_2COSCH(CH_3)_2$ | 25 | 63.2 |
| $C_3H_7SCH_2CH_2COSC_3H_7$ | 25 | 68.5 |
| $C_4H_9SCH_2CH_2COSC_4H_9$ | 50 | 77.2 |
| $CH_3CH_2CH(CH_3)SCH_2CH_2COSCH(CH_3)CH_2CH_3$ | 50 | 72 |
| $(CH_3)_2CHCH_2SCH_2CH_2COSCH_2CH(CH_3)_2$ | 50 | 77.2 |
| $(CH_3)_2CHSOCH_2CH_2COSCH(CH_3)_2$ | 12.5 | 22.7 |
| $(CH_3)_2CHCH_2SOCH_2CH_2COSCH_2CH(CH_3)_2$ | 12.5 | 17.9 |
| $CH_3CH_2CH(CH_3)SO_2CH_2CH_2COSCH(CH_3)CH_2CH_3$ | 12.5 | 33 |
| $(CH_3)_2CHCH_2SO_2CH_2CH_2COSCH_2CH(CH_3)_2$ | 12.5 | 42 |
| $C_3H_7SOCH_2CH_2COSC_3H_7$ | 100 | 73 |
| $CH_3CH_2CH(CH_3)SOCH_2CH_2COSCH(CH_3)CH_2CH_3$ | 100 | 90.5 |
| $C_4H_9SOCH_2CH_2COSC_4H_9$ | 100 | 73 |

The use of compounds of the general formula (I) in which

X represents hydrogen, alkyl, alkoxy, alkylthio, alkylsulphinyl, alkylsulphonyl or a mercapto group, the abovementioned alkyl and alkoxy groups in each case containing 1 to 4 carbon atoms;

Y represents the grouping

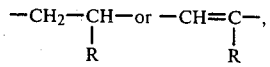

wherein
R denotes hydrogen or alkyl with 1 to 4 carbon atoms, and
Z represents hydroxyl, alkoxy or alkylthio with in each case 1 to 4 carbon atoms in the alkoxy and alkyl radical,
is of particular interest.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the abovementioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 20 to 800, preferably 100 to 500, mg of active ingredient. An individual administration preferably contains the active compound or compounds in amounts of 10 to 30, preferably 50 to 200, mg/dose.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably parenterally. Preferred pharmaceutical compositions and medicaments are therefore those adapted for administration such as parenteral administration. Administration in the method of the invention is preferably parenteral administration.

In general it has proved advantageous to administer amounts of from 0.4 mg to 16 mg/kg, preferably 2 mg to 10 mg/kg, of body weight per day to achieve effective results. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the made in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples illustrate the preparation of compounds of formula (I).

EXAMPLE 1

S-Methyl 3-methylsulphinylpropionothioate $$CH_3SO—CH_2—CH_2—COSCH_3$$

3 g (0.02 mol) of S-methyl 3-methylthiopropionothioate are dissolved in a mixture of 200 ml of water and 160 ml of acetone, 3 drops of glacial acetic acid are added, 2.83 ml of 30% strength hydrogen peroxide solution are added dropwise in the course of 5½ hours and the mixture is kept overnight. The reaction solution is then evaporated in vacuo and the oily residue is kept at 5° C. for seven days. The partially crystalline sludge is taken up in ethyl acetate and chromatographed on silica gel. 0.75 g (22.6% of theory) of S-methyl 3-methylsulphinylpropionothioate is thus obtained as an oil.

$C_5H_{10}O_2S_2$ (166.3)—calculated: C 36.12%, H 6.06%, S 38.57%; found: C 36.06%, H 5.99%, S 38.54%.

EXAMPLE 2

S-Methyl 3-methylsulphonylpropionothioate $$CH_3SO_2CH_2CH_2COSCH_3$$

The compound is obtained as the more rapidly migrating fraction in the chromatography in Example 1. Melting point 72° to 73° C.; yield: 0.5 g (13% of theory).

$C_5H_{10}O_3S_2$ (182.267)—calculated: C 32.95%, H 5.53%, S 35.18%; found: C 32.99%, H 5.51%, S 35.18%.

EXAMPLE 3

S-Methyl 3-methoxypropionothioate $$CH_3OCH_2—CH_2COSCH_3$$

A solution of 41.2 g (0.2 mol) of dicyclohexylcarbodiimide in 40 ml of methylene chloride is added to a solution of 20.8 g (0.2 mol) of 3-methoxypropionic acid in 60 ml of methylene chloride and after the mixture has been cooled to $-10°$ C., 12 ml (0.22 mol) of methanethiol (precooled with acetone/$CO_2$) are added. After leaving the mixture to stand at room temperature for 15 hours, excess dicyclohexylcarbodiimide is destroyed by adding 2 ml of 50% strength acetic acid, the reaction solution is stirred and shortly afterwards the urea which has precipitated is filtered off. The filtrate is washed with water, dried and distilled in vacuo.

9.1 g (34% of theory) of S-methyl 3-methoxypropionothioate are obtained as a yellowish oil of boiling point$_{12-13}$ 65° to 70° C.

$C_5H_{10}O_2S$ (134.201)—calculated: C 44.75%, H 7.51%, S 23.89%; found: C 44.87%, H 7.46%, S 23.73%.

EXAMPLE 4

Ethyl 3-methylthiopropionate $$CH_3SCH_2CH_2COCH_2CH_3$$

A mixture of 20 g (0.2 mol) of ethyl acrylate in 100 ccs (0.25 mol) of tetrahydrofurane and 2.35 g (21 mmols) of potassium tert.-butylate is kept in a laboratory autoclave at room temperature for 8 days and then at 50° C. for 4 hours. The reaction mixture is filtered, the filtrate is evaporated in vacuo and the highly mobile oil which remains is distilled. Boiling point$_{12}$ 84°-86° C.; yield: 24.1 g (81.5% of theory). (Literature boiling point$_{18}$ 88° C.)

GENERAL PREPARATION INSTRUCTIONS FOR S-ALKYL 3-ALKYLTHIOPROPIONOTHIOATES

EXAMPLE 5

S-Methyl 3-methylthiopropionothioate $$CH_3SCH_2CH_2COSCH_3$$

A solution of 8 g (0.2 mol) of NaOH in 160 ccs of water is cooled to $-10°$ C., a 25 ccs ampoule (0.466 mol) of methylmercaptan, cooled in acetone/dry ice, is added and 18.1 g=15.8 ccs (0.2 mol) of acryloyl chloride are then added in portions. After the final addition, the mixture is stirred at room temperature for 2 hours and is then left to stand overnight.

The oil which has separated out is separated off, the aqueous phase is extracted by shaking with ether and the oil phase and ether phase are combined, dried over $Na_2SO_4$ and fractionated. Boiling point$_{20}$ 114°–117° C.; yield: 24.3 g (81% of theory), slightly yellowish oil.

$C_5H_{10}OS_2$ (150.267)—calculated: C 39.97%, H 6.71%, S 42.68%; found: C 40.20%, H 6.63%, S 42.50%.

The following compounds are prepared in a similar manner:

EXAMPLE 6

S-Ethyl 3-ethylthiopropionothioate $$C_2H_5SCH_2CH_2COSC_2H_5$$

Boiling point$_{55}$ 157°–160° C.; yield: 67.4% of theory.
$C_7H_{14}OS_2$(178.3)—calculated: C 47.15%, H 7.91%, S 35.96%; found: C 47.30%, H 7.85%, S 35.91%.

EXAMPLE 7

S-Propyl 3-propylthiopropionothioate $$C_3H_7SCH_2CH_2COSC_3H_7$$

Boiling point$_{0.08}$ 78°–80° C.; yield: 78% of theory.
$C_9H_{18}OS_2$ (206.4)—calculated: C 52.38%, H 8.79%, S 31.08%; found: C 52.47%, H 8.83%, S 30.97%.

EXAMPLE 8

S-Isopropyl 3-isopropylthiopropionothioate $$(CH_3)_2CHSCH_2CH_2COSC(CH_3)_2$$

Boiling point$_{0.15}$ 82°–83° C.; yield: 70% of theory.
$C_9H_{18}OS_2$ (206.4)—calculated: C 52.38%, H 8.79%, S 31.08%; found: C 52.36%, H 8.66%, S 30.95%.

EXAMPLE 9

S-Butyl 3-butylthiopropionothioate $$C_4H_9SCH_2CH_2COSC_4H_9$$

Boiling point$_{0.15}$ 95°–102° C.; yield: 80% of theory.
$C_{11}H_{22}OS_2$ (234.4)—calculated: C 56.36%, H 9.46%, S 27.36%; found: C 56.40%, H 9.44%, S 27.48%.

EXAMPLE 10

S-sec.-Butyl 3-sec.-butylthiopropionothioate $$CH_3CH_2CH(CH_3)SCH_2CH_2COSCH(CH_3)CH_2CH_3$$

boiling point$_{0.2}$ 101°–105° C.; yield: 69% of theory.
$C_{11}H_{22}OS_2$ (234.4)—calculated: C 56.36%, H 9.46%, S 27.36%; found: C 56.30%, H 9.46%, S 27.35%.

EXAMPLE 11

S-tert.-butyl 3-tert.-butylthiopropionothioate $$(CH_3)_3CSCH_2CH_2COSC(CH_3)_3$$

Boiling point$_{28}$ 160°–162° C. (literature boiling point$_{11}$ 135°–136°); yield: 50% of theory.
$C_{11}H_{22}OS_2$(234.4)—calculated: C 56.36%, H 9.46%, S 27.36%; found: C 56.48%, H 9.35%, S 27.14%.

EXAMPLE 12

S-Isobutyl 3-isobutylthiopropionothioate $$CH_3CH(CH_3)CH_2SCH_2CH_2COSCH_2CH(CH_3)CH_3$$

Boiling point$_{0.2}$ 107°–110° C.; yield: 64% of theory.
$C_{11}H_{22}OS_2$ (234.4)—calculated: C 56.36%, H 9.46%, S 27.36%; found: C 56.30%, H 9.41%, S 27.40%.

OXIDATION OF THE ABOVE S-ALKYL 3-ALKYLTHIOPROPIONOTHIOATES

METHOD A: IN GLACIAL ACETIC ACID, WITH 1 MOL OF HYDROGEN PEROXIDE

EXAMPLE 13

S-Butyl 3-butylsulphinylpropionothioate $$C_4H_9SOCH_2CH_2CO-SC_4H_9$$

9.37 g (40 mols) of S-butyl 3-butylthiopropionothioate are dissolved in 9 ccs of glacial acetic acid and 4 ccs (40 mmols) of 30% strength hydrogen peroxide are added dropwise, whilst stirring and cooling in an ice bath. After warming the mixture to room temperature, it is allowed to react for 2 hours and then diluted with water and the product is subsequently extracted with methylene chloride. After evaporating off the solvent in vacuo, the residue is chromatographed on silica gel. Small amounts of S-butyl 3-butylthiopropionothioate and S-butyl 3-butylsulphonylpropionothioate are separated off by washing with ether. Subsequent elution with methylene chloride and evaporating off the solvent from the eluate in vacuo gives 5.75 g (57.5% of theory) of oily S-butyl 3-butylsulphinylpropionothioate.

$C_{11}H_{22}O_2S_2$ (250.4)—calculated: C 52.76%, H 8.85%, S 25.61%; found: C 52.99%, H 8.48%, S 24.32%.

The following compounds are prepared in a similar manner:

EXAMPLE 14

S-sec.-Butyl 3-sec.-butylsulphinylpropionothioate $$CH_3CH_2CH(CH_3)SOCH_2CH_2COSCH(CH_3)CH_2CH_3$$

Yield: 89% of theory; oil.
$C_{11}H_{22}O_2S_2$ (250.4)—calculated: C 52.76%, H 8.85%, S 25.61%; found: C 52.84%, H 8.89%, S 25.63%.

EXAMPLE 15

S-Isopropyl 3-isopropylsulphinylpropionothioate $$(CH_3)_2CHSOCH_2CH_2COSCH(CH_3)_2$$

Yield: 62.5% of theory; oil.
$C_9H_{18}O_2S_2$ (222.4)—calculated: C 48.61%, H 8.16%, S 28.84% found: C 48.84%, H 8.00%, S 28.84%.

EXAMPLE 16

S-Propyl 3-propylsulphinylpropionothioate

C₃H₇SOCH₂CH₂COSC₃H₇

Yield: 56.3% of theory; oil.
C₉H₁₈O₂S₂ (222.4)—calculated: C 48.61%, H 8.16%, S 28.84%; found: C 48.58%, H 8.26%, S 28.75%.

EXAMPLE 17

S-Ethyl 3-ethylsulphinylpropionothioate

C₂H₅SOCH₂CH₂COSC₂H₅

Melting point 35.5°–36° C.; yield: 55.4% of theory.
C₇H₁₄O₂S₂ (194.3)—calculated: C 43.27%, H 7.26%, S 33.00%; found: C 43.15%, H 7.30%, S 32.97%.

EXAMPLE 18

S-tert.-Butyl 3-tert.-butylsulphinylpropionothioate

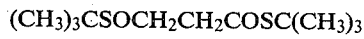
(CH₃)₃CSOCH₂CH₂COSC(CH₃)₃

Melting point 72.5°–73.5° C.; yield: 61.9% of theory.
C₁₁H₂₂O₂S₂ (250.4)—calculated: C 52.76%, H 8.85%, S 25.61%; found: C 52.85%, H 8.70%, S 25.51%.

METHOD B: IN GLACIAL ACETIC ACID, WITH 2 MOLS OF HYDROGEN PEROXIDE, REACTION TIME 3–4 DAYS.

EXAMPLE 19

S-Ethyl 3-ethylsulphinylpropionothioate and S-ethyl 3-ethylsulphonylpropionothioate

C₂H₅SO₂CH₂CH₂COSC₂H₅

7.13 g (40 mmols) of S-ethyl 3-ethylthiopropionothioate are dissolved in 5 ccs of glacial acetic acid, and 8 ccs (80 mmols) of 30% strength hydrogen peroxide are added dropwise, whilst stirring and cooling in an ice bath. The reaction solution is left to react at room temperature for three days, diluted with water and extracted with methylene chloride and the oil which remains after evaporating off the solvent is chromatographed on silica gel.

Elution with ether gives 1.5 g (17.8% of theory) of S-ethyl 3-ethylsulphonyl-propionothioate of melting point 35°–36° C.

C₇H₁₄O₃S₂ (210,32)—calculated: C 39.98%, H 6.71%, S 30.49%; found: C 40.17%, H 6.71%, S 30.40%.

2.8 g (36.1% of theory) of S-ethyl 3-ethylsulphinyl-propionothioate of melting point 35.5°–36° C. are obtained by subsequent elution with acetone.

The following compounds are prepared in a similar manner:

EXAMPLE 20

S-sec.-Butyl 3-sec.-butylsulphonylpropionothioate

CH₃CH₂CH(CH₃)SO₂CH₂CH₂COCH(CH₃)CH₂CH₃ is obtained from S-sec.-butyl 3-sec.-butylthiopropionothioate.

Yield: 31.1% of theory; oil.
C₁₁H₂₂O₃S₂ (266.4)—calculated: C 49.59%, H 8.32%, S 24.07%; found: C 50.35%, H 8.29%, S 23.71%.

In addition: S-sec.-butyl 3-sec.-butylsulphinylpropionothioate Yield: 30% of theory.

EXAMPLE 21

S-Isobutyl 3-isobutylsulphonylpropionothioate

(CH₃)₂CHCH₂SO₂CH₂CH₂COSCH₂CH(CH₃)₂ is obtained from S-isobutyl 3-isobutylthiopropionothioate. Melting point 43°–44° C.; yield: 20% of theory.
C₁₁H₂₂O₃S₂ (266.4)—calculated: C 49.59%, H 8.32%, S 24.07%; found: C 49.70%, H 8.29%, S 24.01%.

In addition: S-isobutyl 3-isobutylsulphinylpropionothioate Yield: 30% of theory; waxy substance.
C₁₁H₂₂O₂S₂ (250.4)—calculated: C 52.76%, H 8.85%, S 25.61%; found: C 52.94%, H 8.91%, S 25.68%.

EXAMPLE 22

S-tert.-Butyl 3-tert.-butylsulphonylpropionothioate

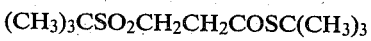
(CH₃)₃CSO₂CH₂CH₂COSC(CH₃)₃ is obtained from tert.-butyl 3-tert.-butylthiopropionothioate. Melting point 98°–99° C.; yield: 22.6% of theory.
C₁₁H₂₂O₃S₂ (266.4)—calculated: C 49.59%, H 8.32%, S 24.07%; found: C 49.47%, H 8.18%, S 24.24%.

In addition: S-tert.-butyl 3-tert.-butylsulphinylpropionothioate Melting point 73°–74° C.; yield: 34% of theory.

If the mixture is not cooled during the dropwise addition of hydrogen peroxide, only 3-tert.-butylsulphonyl-propionic acid is formed, in an exothermic reaction. (CH₃)₃CSO₂CH₂CH₂COOH Melting point 103° C.; yield: 14.2% of theory.

C₇H₁₄O₃S (194.3)—calculated: C 43.28%, H 7.26%, S 16.51%; found: C 43.57%, H 7.33%, S 16.61%.

METHOD C: IN GLACIAL ACETIC ACID, WITH 2 MOLS OF HYDROGEN PEROXIDE; REACTION TIME 10–14 DAYS.

EXAMPLE 23

S-sec.-Butyl 3-sec.-butylsulphonylpropionothioate and

S-sec.-Butylsulphonylpropionic acid

CH₃CH₂CH(CH₃)SO₂CH₂CH₂COOH 9.37 g (40 mmols) of S-sec.-butyl 3-sec.-butylthiopropionothioate are dissolved in 17 ccs of glacial acetic acid, and 8 ccs (~80 mmols) of 30% strength hydrogen peroxide are added dropwise, whilst stirring and cooling in an ice bath. The mixture is allowed to react at room temperature for 14 days and diluted with water, the reaction mixture is extracted with methylene chloride and the oily evaporation residue of the extract is chromatographed on silica gel.

2.35 g (22.2% of theory) of S-sec.-butyl 3-sec.-butylsulphonylpropionothioate are obtained by elution with diisopropyl ether.

Subsequent washing of the column with acetone gives 2 g (25.8% of theory) of 3-sec.-butylsulphonylpropionic acid of melting point 66°–67° C.

C₇H₁₄O₄S (194.3)—calculated: C 43.28%, H 7.26%, S 16.61%; found: C 43.22%, H 7.15%, S 16.66%.

The following compounds are prepared in a similar manner:

EXAMPLE 24

S-Butyl 3-butylsulphonylpropionothioate is obtained from S-butyl 3-butylthiopropionothioate. Melting point 46°–47° C.; yield: 10.4% of theory.

$C_{11}H_{22}O_3S_2$ (266.4)—calculated: C 49.59%, H 8.32%, S 24.07%; found: C 49.82%, H 8.38%, S 23.87%.

In addition: 3-butylsulphonylpropionic acid $C_4H_9SO_2CH_2CH_2COOH$ Melting point 111°–111.5° C.; yield: 24.5% of theory.

$C_7H_{14}O_4S$ (194.3)—calculated: C 43.28%, H 7.26%, S 16.61%; found: C 43.34%, H 7.31%, S 16.48%.

EXAMPLE 25

S-Isobutyl 3-isobutylsulphonylpropionothioate is obtained from S-isobutyl 3-isobutylthiopropionothioate. Melting point 42°–43° C.; yield: 6.1% of theory. In addition: 3-isobutylsulphonylpropionic acid Melting point 106°–107° C.; yield: 11.6% of theory.

$C_7H_{14}O_4S$ (194.3)—calculated: C 43.28%, H 7.26%, S 16.51%; found: C 43.43%, H 7.25%, S 16.48%.

METHOD D: IN AQUEOUS ACETONE, WITH 2 MOLS OF HYDROGEN PEROXIDE.

EXAMPLE 26

S-Isopropyl 3-isopropylsulphonylpropionothioate $(CH_3)_2CHSO_2CH_2CH_2COSCH(CH_3)_2$ and S-isopropyl 3-isopropylsulphinylpropionothioate 4.12 g (20 mmols) of S-isopropyl 3-isopropylthiopropionothioate are dissolved in a mixture of 20 ccs of water and 60 ccs of acetone and after the solution has been cooled to 0° C., a few drops of glacial acetic acid are added and 4 ccs (40 mmols) of 30% strength hydrogen peroxide are added dropwise, whilst stirring. The reaction mixture is kept at room temperature for 8 days, treated with a spatula tip of platinum black in order to destroy excess hydrogen peroxide and filtered, the filtrate is evaporated in vacuo and the residue is chromatographed on silica gel.

1.9 g (39.9% of theory) of S-isopropyl 3-isopropylsulphonylpropionothioate of melting point 45°–47° C. are obtained by elution with ether.

$C_9H_{18}O_3S_2$ (238.4)—calculated: C 45.34%, H 7.62%, S 26.90%; found: C 45.53%, H 7.56%, S 26.80%.

Subsequent elution with acetone gives 1.2 g (27% of theory) of oily S-isopropyl 3-isopropylsulphinylpropionothioate.

The following compound is prepared in a similar manner:

EXAMPLE 27

S-Propyl 3-propylsulphonylpropionothioate $C_3H_7SO_2CH_2CH_2COSC_3H_7$ is obtained from S-propyl 3-propylthiopropionothioate. Melting point 55°–56° C.; yield: 18.5% of theory.

$C_8H_{18}O_3S_2$ (238.4)—calculated: C 45.34%, H 7.62%, S 26.90%; found: C 45.63%, H 7.59%, S 26.91%.

What is claimed is:

1. A compound selected from the group consisting of S-methyl 3-methylsulphinylpropionothioate and S-methyl 3-methoxypropionothioate.

2. A compound of claim 1 which is S-Methyl 3-methylsulphinylpropionothioate.

3. A compound of claim 1 which is S-Methyl 3-methoxypropionothioate.

* * * * *